US00PP37019P2

(12) United States Plant Patent
Courtney

(10) Patent No.: US PP37,019 P2
(45) Date of Patent: Oct. 14, 2025

(54) ***DAMPIERA* PLANT NAMED 'ALTMP2336'**

(50) Latin Name: *Dampiera hybrida*
Varietal Denomination: Altmp2336

(71) Applicant: Botanic Gardens and Parks Authority, West Perth (AU)

(72) Inventor: Patrick Courtney, Beaconsfield (AU)

(73) Assignee: BOTANIC GARDENS AND PARKS AUTHORITY, West Perth (AU)

( * ) Notice: Subject to any disclaimer, the term of this patent is extended or adjusted under 35 U.S.C. 154(b) by 0 days.

(21) Appl. No.: 19/004,826

(22) Filed: Dec. 30, 2024

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

(56) References Cited

PUBLICATIONS

Star Roses and Plants 2025 Catalog, Woody Ornamentals & Edibles (Oct. 7, 2024).

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Dampiera* plant, referred to by its cultivar name, 'Altmp2336', is disclosed. The new variety displays purple-colored flowers with extended flowering. Silver grey-colored foliage is formed. The growth habit is low growing, moderately vigorous and spreading. Additionally, the new variety is particularly well suited for growing as distinctive ornamentation in the landscape.

2 Drawing Sheets

Figure 1:
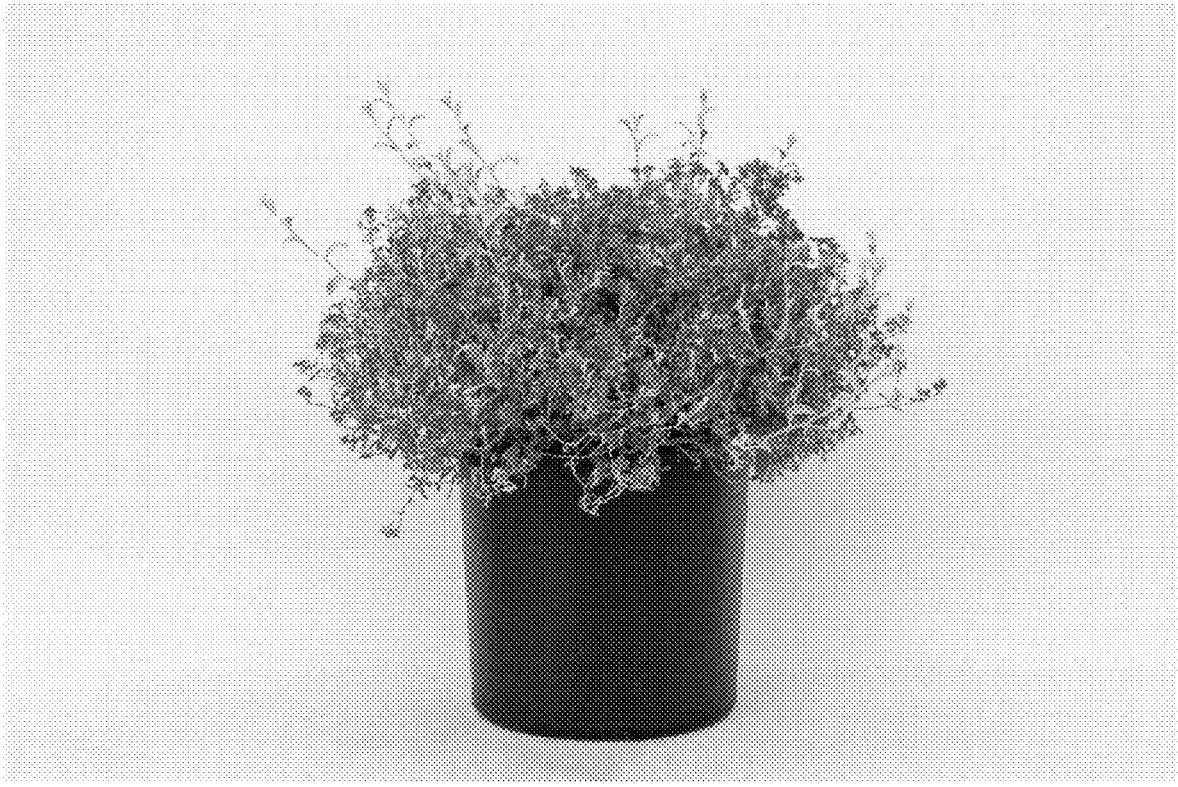

Latin name of genus and species of plant claimed: *Dampiera hybrida.*

Variety denomination: 'Altmp2336'.

STATEMENT REGARDING PRIOR DISCLOSURES BY THE INVENTOR

The first offer for sale of the new variety was Jul. 12, 2024, in the United States of America, at the New Varieties Showcase at the Cultivate Trade Show in Columbus, Ohio, followed by the publication of the 2025 Star Roses and Plants Woody Ornamentals & Edibles Catalog released Oct. 7, 2024. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Dampiera hybrida* plant originated in a controlled breeding program in Perth, Western Australia in March 1999. The objective of the breeding program was to develop new ornamental plant varieties. The new cultivar is the result of cross pollination. The female (seed) parent (unnamed) of the new cultivar is a proprietary breeding selection (not patented). The male (pollen) parent (unnamed) of the new cultivar is a different proprietary breeding selection (not patented).

The parentage of the new variety can be summarized as follows:

proprietary breeding selection x different proprietary breeding selection

The seeds resulting from the above cross pollination were sown and small plants were obtained which were physically and biologically different from each other. The new cultivar was selected as a single flowering plant during September 1999, in a controlled environment in Perth, Western Australia.

The new variety has been found to undergo asexual propagation by terminal stem cuttings and in vitro propagules in Perth, Western Australia. Asexual propagation by terminal stem cuttings and in vitro propagules in Perth, Western Australia has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Dampiera* plant of the present invention possesses the following combination of characteristics:

(a) forms purple-colored flowers,
(b) displays silver grey-colored foliage, and
(c) exhibits a low growing, moderately vigorous, spreading growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the new variety displays darker purple-colored flowers and extended flowering compared to the lilac purple-colored flowers of the female proprietary breeding selection parent (i.e., the seed parent). Additionally, the new variety forms flowers that are lighter purple in color and exhibits a more spreading habit compared to the different proprietary breeding selection (i.e., the pollen parent), which forms deep purple-colored flowers and exhibits a bushy growth habit. Moreover, the new variety can be readily distinguished from non-parental related similar varieties. For example, the new variety exhibits a more spreading habit, forms lighter purple-colored flowers and displays extended flowering compared to plants of the straight species *Dampiera incana*.

The new variety has been named 'Altmp2336'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Altmp2336' variety. The photographed plants were approximately one year old and grown in three-gallon containers in Cochranville, Pennsylvania. The photographs were taken in November 2020.

FIG. 1—illustrates a specimen of the plant, displaying the overall growth and flowering habit—side view.

Figure 2:
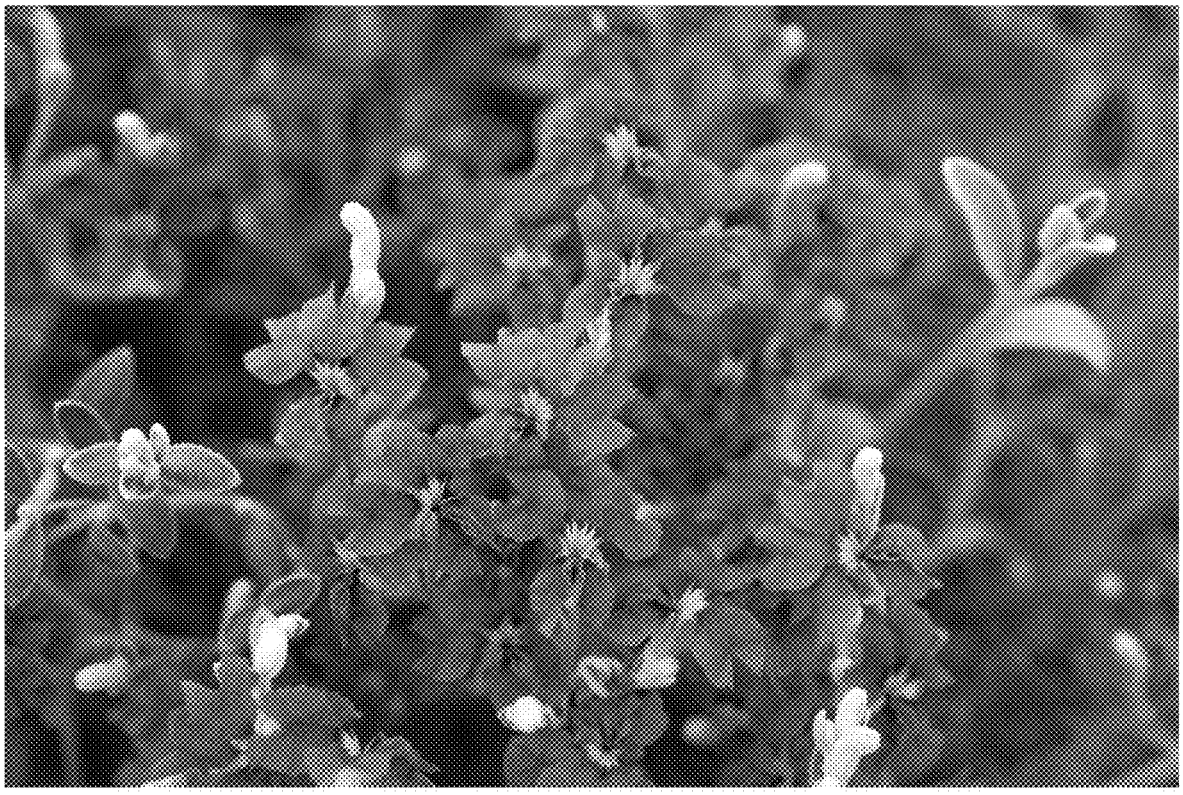

FIG. 2—illustrates a specimen of an inflorescence from a plant of the new variety—close-up view.

DETAILED BOTANICAL DESCRIPTION

The chart used in the identification of the colors is that of The Royal Horticultural Society (R.H.S. Colour Chart), 2015 edition, London, England. The terminology which precedes reference to the chart has been added to indicate the corresponding color in more common terms and The R.H.S. Colour Chart designation used herein represents the closest color observed on the majority of the specified botanical feature. The color values were determined in November 2023, under natural light conditions in Cochranville, Pennsylvania. The description is based on the observation of plants produced from cuttings from stock plants and grown in three-gallon containers for approximately one year in an outdoor nursery in Cochranville, Pennsylvania. Plants were pinched once after transplant.

Botanical classification: *Dampiera hybrida* cultivar 'Altmp2336'.

Propagation:

- *Type cutting*.—Terminal stem cuttings.
- *Time to initiate roots*.—Approximately 35 to 42 days on average.
- *Time to produce a rooted cutting*.—Approximately 56 to 60 days on average.
- *Root description*.—Fibrous.
- *Rooting habit*.—Freely branching.

Plant:

- *Habit*.—Low growing, moderately vigorous spreading growth habit.
- *Commercial crop time*.—Approximately 4 months from a rooted cutting to finish in a 3-gallon container on average.
- *Hardiness*.—USDA Zones 8-11.
- *Size*.—Typically 18.0 cm to 24.0 cm in height from soil level to top of plant plane; and typically 50.0 cm to 70.0 cm in width from soil level to apices of lateral branches.

Branches:

- *Branching habit*.—Freely branching habit.
- *Quantity of lateral branches per plant*.—Approximately 25.
- *Shape*.—Round.
- *Strength*.—Strong.
- *Size*.—Length, lateral branches: typically 22.0 cm to 35.0 cm. — diameter, lateral branches: approximately 2.1 mm on average. — length, main branches: typically 48.0 cm to 60.0 cm. — diameter, main branches: approximately 3.6 mm on average. — internode length: typically 2.0 cm to 4.0 cm.
- *Texture*.—Pubescent.
- *Color*.—Greyed-Green Group 191A to Greyed-Green Group 191C.

Foliage:

- *Number of leaves*.—Approximately 15-26 per branch.
- *Fragrance*.—Absent.
- *Form*.—Simple.
- *Arrangement*.—Alternate, simple, sessile.

Leaves:

- *Aspect*.—Erect to about 45° from the branch axis.
- *Shape*—General: oblanceolate. — margin: entire. — apex: rounded. — base: attenuate.
- *Venation*.—One single major vein.
- *Size*.—Length: typically 2.5 cm to 3.5 cm. — width: typically 1.0 cm to 1.3 cm.
- *Texture*.—Upper surface: pubescent. — lower surface: pubescent.
- *Color*.—Upper and lower surface of developing leaves: Greyed-Green Group 191C with venation of Yellow-Green Group 147C. — upper and lower surface of fully expanded leaves: Yellow-Green Group 147B with venation of Yellow-Green Group 147C.

Inflorescence:

- *Type*.—Zygomorphic.
- *Shape*.—Fan-shaped, with 5 petals that form two groupings; the top three petals are fused, and the bottom two petals are fused.
- *Depth*.—Approximately 8.0 mm.
- *Width*.—Approximately 1.4 cm.
- *Flower quantity*.—Typically 8 to 12 open flowers per inflorescence.
- *Habit*.—Solitary flowers arise from leaf axils with one flower per axil; flowers held outwardly on upturned lateral apices; freely flowering.
- *Persistent or self-cleaning*.—Not persistent.
- *Lastingness of individual flower*.—Typically two weeks.
- *Fragrance*.—None detected.
- *Bud*.—Shape: elliptic. — length: typically 5.0 mm to 8.0 mm. — diameter: approximately 2.0 mm on average. — color: Violet-Blue Group 93B.

*Perianth*.—Aspect: fan-shaped. — length, fan: approximately 1.5 cm on average. — width, fan: approximately 1.7 cm on average.

*Petals*.—Quantity: 5. — shape: orbicular. — arrangement: three petals fused at base, facing up to form a fan shape, and two fused together facing downward. — margin: entire. — apex: obcordate. — base: petals are fused at the base to form a tabular throat. — length: approximately 6.0 mm on average. — width: approximately 5.0 mm on average. — texture of upper and lower surfaces: smooth. — color, when fully opened (petal): Violet-Blue Group 93B; color, when fully opened (throat): Yellow Group 2B.

*Sepals*.—Quantity per flower: 3; one large sepal and two smaller sepals lateral to larger sepal. — length, larger sepal: approximately 1.2 cm on average. — width, larger sepal: approximately 3.0 mm on average. — length, lateral sepals: approximately 7.0 mm on average. — width, lateral sepals: approximately 1.7 mm on average. — shape: larger sepal is tridentate and lateral sepals are falcate. — apex: acute. — base: fused. — margin: entire. — texture, upper surface: pubescent. — texture, lower surface: pubescent. — color: Greyed-Green Group 194D.

*Reproductive organs*.—

*Androecium*.—Stamen quantity per flower: approximately 5 on average. — filament length: approximately 1.0 mm on average. — filament color: Greyed-Green Group 193B. — anther shape: oblong. — anther length: approximately 1.0 mm on average. — anther diameter: approximately 0.7 mm on average. — anther color: Violet Group N88D. — pollen amount: sparse. — pollen color: White Group 155A.

*Gynoecium*.—Pistil quantity per flower: 1. — pistil length: approximately 5.0 mm on average. — stigma shape: elongate. — stigma color: Violet Group 86A. — style length: approximately 3.0 mm on average. — style color: Yellow-Green Group 145B. — ovary diameter: 0.5 mm. — ovary color: Yellow-Green Group 145B.

Development:

*Blossoming*.—Late spring through fall; may blossom all year in a greenhouse setting with regular trims.

*Seed and fruit production*.—Neither seed nor fruit production have been observed.

*Resistance to disease and pests*.—Neither resistance nor susceptibility to normal diseases and pests of *Dampiera* have been observed.

The new 'Altmp2336' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Dampiera* plant named 'Altmp2336' characterized by the following combination of characteristics:

(a) forms purple-colored flowers, (b) displays silver grey-colored foliage, and (c) exhibits a low growing, moderately vigorous, spreading growth habit;

substantially as herein shown and described.

* * * * *